United States Patent
Callahan et al.

(10) Patent No.: US 12,060,565 B1
(45) Date of Patent: Aug. 13, 2024

(54) ENDOCARP-SPECIFIC PROMOTER AND USES THEREOF

(71) Applicant: The United States of America, as represented by The Secretary of Agriculture, Washington, DC (US)

(72) Inventors: Ann M. Callahan, Shepherdstown, WV (US); Christopher D. Dardick, Charles Town, WV (US)

(73) Assignee: The United States of America, as Represented by the Secretary of Agriculture, Washington, DC (US)

(*) Notice: Subject to any disclaimer, the term of this patent is extended or adjusted under 35 U.S.C. 154(b) by 0 days.

(21) Appl. No.: 18/184,404

(22) Filed: Mar. 15, 2023

(51) Int. Cl.
  *C12N 15/82* (2006.01)
(52) U.S. Cl.
  CPC ................. *C12N 15/8234* (2013.01)
(58) Field of Classification Search
  None
  See application file for complete search history.

(56) References Cited

U.S. PATENT DOCUMENTS

| | | |
|---|---|---|
| 11,091,768 B2 | 8/2021 | Thomson |
| 2022/0042027 A1 | 2/2022 | Thomson |

OTHER PUBLICATIONS

Sorkina et al., Isolation of a citrus promoter specific for reproductive organs and its functional analysis in isolated juice sacs and tomato, 2011, Plant Cell Reproduction, vol. 30, pp. 1627-1640. (Year: 2011).*

Bilas et al., Cis-regulatory elements used to control gene expression in plants, 2016, Plant Cell Tissue Organ Culture, vol. 127, pp. 269-287. (Year: 2016).*

Doelling et al., The minimal ribosomal RNA gene promoter of Arabidopsis thaliana includes a critical element at the transcription initiation site, 1995, The Plant Journal, vol. 8(5), pp. 683-692. (Year: 1995).*

GenBank, Accession No. AP019303, Prunus dulcis DNA, pseudomolecule Pd07 (Year: 2019).*

Deikman et al., Organization of ripening and ethylene regulatory regions in a fruit-specific promoter from tomato (*Lycopersicon esculentum*), (1992), Plant Physiology, vol. 100, pp. 2013-2017. (Year: 1992).*

Sanchez-Perez et al., Mutation of a bHLH transcription factor allowed almond domestication, (2019), Science, vol. 364, pp. 1095-1098. (Year: 2019).*

CD Dardick, et al., 2010, "Stone Formation in Peach Fruit Exhibits Spatial Coordination of the Lignin and Flavonoid Pathways and Similarity to Arabidopsis Dehiscence," BMC Biol. 8:13. https://doi.org/10.1186/1741-7007-8-13.

* cited by examiner

*Primary Examiner* — Cathy Kingdon Worley
*Assistant Examiner* — Christina L Meadows
(74) *Attorney, Agent, or Firm* — John Fado; Maria Restrepo-Hartwig (57) ABSTRACT

The disclosure relates to polynucleotides comprising an endocarp-specific promoter sequence from the peach peroxidase (POX) gene operably linked to a heterologous nucleotide sequence encoding a product of interest. The polynucleotides can be used to specifically alter endosperm gene expression in fruit. In a transgenic cell, the polynucleotides may block formation of phenylpropanoid pathway lignin-pathway precursors, formation of lignin monomers, and/or polymerization of lignin monomers.

18 Claims, 9 Drawing Sheets
(4 of 9 Drawing Sheet(s) Filed in Color)
Specification includes a Sequence Listing.

```
ATGGATGTTGTAATCTCAAGTTATCAGCTGAAATCAATATAGATCTCTTGCTCAT
TAATTTGTCATCTGCGACTTGGAAAGCTATTAGCAAAGTTGCTAAGGGATATACG
AGCTATGATGGCATATGCTCTTTTCTTTGAGGCCTGTAAGATGTCACTTGCAAAT
TTACAAATGAGGAATCAGAGCCTTAAAGGAGTTGTTCTCCAACCCCGCTTATAAT
ATCTTTTATCATATTTGGATCTTCCAGATTAACCTAATATTCCCGTTATCATACT
TGATTATAATTTAACTTTTCTTCATGCCTCCATACGCGTTTAACACACAATGACA
ATTTATTTACTAATATTGTCGATCCTGAAGTCAAAAGCCACAAAATAAAGGAAT
CAATGTCAATTCATGGATAGTAGGGGGAAGAAAAAGAACAAGAAAGAAGACAGGA
GATGAATATTAGGTGTAAAGAAATGTTAAAGGGCAGTCGCCTATCCAAGTGGACA
ACTCTCAGTTGTTGATACGTGGGGGGCTCGTGAGCTTGCATCATTAAAATCCAT
ACAATGAACATCTAGACGGCCATTAAATTTCAATGTGAACGTTAGGGGAAAGGGG
AAAAAGTGCCCAAGTATGAAGGGTTCAACCCTAATTTTGTGGCTTGCTCTAAGAT
ACCTTTACAGACATTGACAATGTCAGAAGCTTTGAGTCATCTAGTTTAGTTTGGG
TAACTATATACTCTGTCAAACACAGTAGTTGAGTCTGCTCCTACTCTCTCTTTAT
TGTCATCACAAAACAATTAACAAAAGGTTGACCTGCTTCTGTTCCACATGGAATC
GGTAGTCAATTGCAATGCTGTGATCCAATAACACGTGGGACGGTGAAATGTTTGC
TTAACATATTTGACAAGAATTACCCAACAAAATTTGGGAATCATTTTGAAAGTTA
CACAAGGTTTTTTATAATTATTTTTATTTATACAAGCGATATTAAGAGAGGGGA
GAATAGAACCTAGGATTGCATGTGCAAGGGTAAATGTTTTTAACCACTTGAGCTA
GTTTTAACTTAAGAAAGAGTGTTAGAAGAACCCTAATGTAGAACTCTAGCCAAA
GTTCAAATTTTCTTATTAATCTTCAATACATGGAAAATTACATTAATGGACCTTC
CAAATGCTTGCTAACACGTTATTCTAATTGGAATTTTCTGAGACCGAGATCTAAA
TGAAGGTGGGATGTTGTTGTAATCAATTAATGGAAATTGCTTAACTGATGATCTA
AAGGCCCACTGTACTGATAATTTTTCTATGTCAAGGATACTTGGATTATAAGCC
AAAAAGGTTTGTTCTTCTATAATGAGCTGATTGAGCTTAGATCTTGTATTAACAT
GATGATTAGTCACCCCAAAGAATGAAAGCTTTGTACCAACTCCAACCTTCTCTTC
TGATCCTGTCTATTGATGTAGCTACCGAAAGTAAGTTACCAACTCCAGCTTCTCT
ATACCTCACTCTTGAAAGTTGTGTACAAAGTCTCCTCTATAAATACTCCCTAAGC
CATCCCAACATTCATCAAAGCAAGTCTTGGGGAGAGCTTTATTTTCATTTGACAA
TTTCAAGTCTTCTTCTTCTCTAGTGGTCTTACTAGACTTGAACTAAGGGTACCCC
AAAAAAAACATT
```

'HoneySweet'  
(Positive Control)     POX::UIDA 1-year wood

SEQUENCE LISTING

```
Sequence total quantity: 1
SEQ ID NO: 1            moltype = DNA  length = 1662
FEATURE                 Location/Qualifiers
source                  1..1662
                        mol_type = genomic DNA
                        organism = Prunus persica
SEQUENCE: 1
atggatgttg taatctcaag ttatcagctg aaatcaatat agatctcttg ctcattaatt  60
tgtcatctgc gacttggaaa gctattagca aagttgctaa gggatatacg agctatgatg 120
gcatatgctc ttttctttga ggcctgtaag atgtcacttg caaatttaca aatgaggaat 180
cagagcctta aaggagttgt tctccaaccc cgcttataat atcttttatc atatttggat 240
cttccagatt aacctaatat tcccgttatc atacttgatt ataatttaac tttcttcat  300
gcctccatac gcgtttaaca cacaatgaca atttatttac taatattgtc gatcctgaag 360
tcaaaaagcc acaaaataaa ggaatcaatg tcaattcatg gatagtaggg ggaagaaaaa 420
gaacaagaaa gaagacagga gatgaatatt aggtgtaaag aaatgttaaa gggcagtcgc 480
ctatccaagt ggacaactct cagttgttga tacgtggggg ggctcgtgag cttgcatcat 540
```

-continued

```
taaaatccat acaatgaaca tctagacggc cattaaattt caatgtgaac gttaggggaa 600
aggggaaaaa gtgcccaagt atgaaggggtt caaccctaat tttgtggctt gctctaagat 660
acctttacag acattgacaa tgtcagaagc tttgagtcat ctagtttagt ttgggtaact 720
atatactctg tcaaacacag tagttgagtc tgctcctact ctctctttat tgtcatcaca 780
aaacaattaa caaaaggttg acctgcttct gttccacatg gaatcggtag tcaattgcaa 840
tgctgtgatc caataacacg tgggacggtg aaatgtttgc ttaacatatt tgacaagaat 900
tacccaacaa aatttgggaa tcattttgaa agttacacaa ggttttttta taattatttt 960
tatttataca agcgatatta agagagggga gaatagaacc taggattgca tgtgcaaggg 1020
taaatgtttt taaccacttg agctagtttt aacttaagaa aagagtgtta gaagaaccct 1080
aatgtagaac tctagccaaa gttcaaattt tcttattaat cttcaataca tggaaaatta 1140
cattaatgga ccttccaaat gcttgctaac acgttattct aattggaatt ttctgagacc 1200
gagatctaaa tgaaggtggg atgttgttgt aatcaattaa tggaaattgc ttaactgatg 1260
atctaaaggc ccactgtact gataattttt tctatgtcaa ggatacttgg attataagcc 1320
aaaaaggttt gttcttctat aatgagctga ttgagcttag atcttgtatt aacatgatga 1380
ttagtcaccc caaagaatga aagctttgta ccaactccaa ccttctcttc tgatcctgtc 1440
tattgatgta gctaccgaaa gtaagttacc aactccagct tctctatacc tcactcttga 1500
aagttgtgta caaagtctcc tctataaata ctccctaagc catcccaaca ttcatcaaag 1560
caagtcttgg ggagagcttt attttcattt gacaatttca agtcttcttc ttctctagtg 1620
gtcttactag acttgaacta agggtacccc aaaaaaaaca tt                  1662
```

ENDOCARP-SPECIFIC PROMOTER AND USES THEREOF

FIELD OF THE INVENTION

The present disclosure relates generally to the field of plant breeding and biotechnology. More specifically, it relates to an endocarp-specific promoter, and uses thereof.

SEQUENCE LISTING

The instant application contains a Sequence Listing XML required by 37 C.F.R. § 1.831(a) which has been submitted in XML file format via the USPTO patent electronic filing system, and is hereby incorporated by reference in its entirety. The XML file was created on Mar. 11, 2023, is named Sequence Listing-008022.xml, and has 3.18 KB.

BACKGROUND OF THE INVENTION

Stone fruits such as cherries, plums, and apricots have pits consisting of a seed surrounded by a thick shell that is derived from lignification and hardening of the fruit endocarp tissue layer. The woody stone tissue presents a significant impediment to the development of seedless fruit. It also limits the use of stone fruits in many processed products such as granola bars and cereals due to the presence of fragments of stone tissue after mechanical pitting.

Up to now, no endocarp-specific promoters have been identified for stone fruits or other plant species. A number of genes have been identified that are expressed in endocarp tissues and play known roles in lignification (laccases, NACs) or tissue differentiation (SHP, STK, FUL). However, these genes are not shown to be specific to the endocarp only since they have some expression in other tissues.

There are many production processes that could be positively impacted by the elimination of endocarp tissue. Pitting machines have been designed for specific crops including, but not limited to, stone fruit (cherries, plums, peaches, apricots) olives, dates, and mangoes. These also require confirmation processes to measure the quantity of pit fragments which are highly regulated. This is a major expense for all processing industries. In addition, other crops with a hardened endocarp are also subject to processing to eliminate that endocarp such as hulling coffee beans (parchment beans) and winnowing cocoa beans. Technology to soften and/or eliminate the hardened endocarp would have the potential to save significant production costs and expand markets for processed fruit. Similarly, improving shell qualities for nuts such as almonds will result in easier processing.

Thus, there is significant commercial interest in developing seedless fruit and nuts with improved shell qualities, and identification of an endocarp-specific promoter will assist in the preparation of transgenic plants with altered endocarp gene expression only within the stone tissue.

SUMMARY OF THE INVENTION

Provided herein is an endocarp-specific promoter, and methods of using such promoter to produce plants with altered stone tissue without negatively impacting plant growth or fruit production.

In an embodiment, the disclosure relates to a polynucleotide comprising an endocarp-specific promoter sequence, or a biologically-active fragment thereof operably linked to a heterologous nucleotide sequence encoding a product of interest. In some embodiments of the invention the endocarp-specific promoter has a nucleotide sequence at least 90% identical to SEQ ID NO: 1 or a biologically active fragment thereof. In some embodiments of the disclosure the product of interest encoded by the heterologous nucleotide sequence operably linked to an endocarp-specific promoter is an RNA molecule or a polypeptide. In some embodiments of the disclosure, the product of interest encoded by the heterologous nucleotide sequence operably linked to an endocarp-specific promoter is in the lignin biosynthetic pathway. In some embodiments of the disclosure, the polynucleotide is comprised within a vector, a host cell, a plant, or a plant part.

In an embodiment, the disclosure relates to a method for modifying endocarp development in a fruit of a plant. The method comprises transforming a plant cell with a polynucleotide comprising an endocarp-specific promoter sequence, or a biologically-active fragment thereof operably linked to a heterologous nucleotide sequence encoding a product of interest, regenerating a plant from the transformed plant cell, and growing the regenerated plant to produce fruit with modified endocarp development. In some embodiments of the disclosure, the fruit from the transformed plant has little or no lignin.

In some embodiments, the disclosure relates to drupe plants with modified endocarp. In some embodiments of the disclosure, the drupe plants with modified endocarp are plum, peach, nectarine, apricot, date, mango, cherry, almond, coffee, jujube, oil palm, pistachio, damson, olive, coconut, holly fruit, elder fruit, mulberry, blackberry, or raspberry.

BRIEF DESCRIPTION OF THE DRAWINGS

The patent or application file contains at least one drawing executed in color. Copies of this patent or patent application publication with color drawing(s) will be provided by the office upon request and payment of the necessary fee.

Advantages of embodiments of the present invention will be apparent from the following detailed description of the exemplary embodiments. The following detailed description should be considered in conjunction with the accompanying figures in which:

FIG. 3A and FIG. 3B depicts the qPCR fruit-tissue specific detection of the peroxidase gene (POX) from 30 days after budding (DAB) to just prior stone hardening.

FIG. 6A to FIG. 6C depict schematic diagrams of the hairpin constructs used to block expression of enzymes in pathways leading to hardened-polymerized lignin.

FIG. 8A and FIG. 8B depict images of the mixed block of transgenic plum plants expressing POX::UIDA as well as those expressing the ST1-3 construct, the hairpin arrangements of lignin pathway genes.

FIG. 9A to FIG. 9C depict images of transgenic plums expressing the STL1, STL2, or STL3 constructs that resulted in noticeably altered stone tissue.

DETAILED DESCRIPTION

The instant disclosure relates to the identification of a promoter that drives expression specifically in the plant endocarp tissue layer. The promoter identified herein is useful to drive expression of gene constructs that can change the properties of the endocarp in drupe plants.

Lignin is one of the most important secondary metabolite which is produced by the phenylalanine/tyrosine metabolic pathway in plant cells. Lignin biosynthesis is a complex network. After a series of steps involving deamination, hydroxylation, methylation, and reduction, monolignols are produced in the cytoplasm and transported to the apoplast. In the secondary wall lignin is polymerized by peroxidase (POD) and laccase (LAC) from at least three main types of monolignols (sinapyl alcohol, S unit; coniferyl alcohol, G unit, and p-coumaryl alcohol, H unit). Several compounds including hydroxycinnamaldehydes, tricin flavones, hydroxystilbenes, and xenobiotics have also been recognized as lignin subunits.

The lignin biosynthesis pathway in higher plants includes phenylalanine ammonia-lyase (PAL); tyrosine ammonia-lyase (TAL); cinnamate 4-hydroxylase (C4H); 4-coumarate: CoA ligase (4CL); cinnamoyl-CoA reductase (CCR); hydroxycinnamoyl-CoA shikimate/Quinatehydroxycinnamoyltransferase (HCT); p-coumarate 3-hydroxylase (C3H); caffeoyl-CoA O-methyltransferase (CCoAOMT); ferulate 5-hydroxylase (F5H); caffeoyl shikimate esterase (CSE); caffeic acid O-methyltransferase (COMT); cinnamyl alcohol dehydrogenase (CAD); laccase (LAC); and peroxidase (POX).

The present disclosure provides promoters that are capable of directing endocarp-specific expression in drupe plants. In an embodiment, the disclosure relates to a polynucleotide comprising an endocarp-specific promoter sequence, or a biologically-active fragment thereof operably linked to a heterologous nucleotide sequence encoding a product of interest. In some embodiments, the disclosure relates to a polynucleotide comprising an endocarp-specific promoter sequence at least 90% identical to SEQ ID NO: 1 or a biologically active fragment thereof operably linked to a heterologous nucleotide sequence encoding a product of interest. In some embodiments of the disclosure, the endocarp-specific promoter comprises a nucleotide sequence of SEQ ID NO: 1.

Drupe is a botanical term for a type of fleshy fruit in which the seed is enclosed in a single shell of hardened endocarp enclosed by an outer fleshy part (mesocarp), which in turn is surrounded by a thin skin (exocarp). These fruits develop from a single carpel, and mostly from flowers with superior ovaries. The definitive characteristic of a drupe is that the hard, lignified pit is derived from the ovary wall of the flower. Among flowering plants that produce drupes are coffee, jujube, mango, olive, most palms (including date, coconut, and oil palms), pistachio, and all members of the genus *Prunus*, including almond, apricot, cherry, damson, nectarine, peach, and plum. The bony pit is sometimes known as a "stone," and thus these fruits are often referred to as stone fruits.

In some embodiments, the product of interest encoded by the heterologous nucleotide sequence operably linked to an endocarp-specific promoter sequence, or a biologically-active fragment thereof is an RNA molecule or a polypeptide. The encoded RNA molecule may form a hairpin loop that can cause transcriptional silencing of a desired product in the lignin biosynthetic pathway. At least a portion of the encoded RNA molecule may be from a POX gene intron, assisting in the formation of the hairpin. In some embodiments of the disclosure, the product of interest blocks formation of at least one lignin precursor in the lignin pathway, blocks formation of at least one type of lignin monomer, or blocks polymerization of lignin molecules.

In some embodiments, the disclosure relates to a vector comprising a polynucleotide of the invention. The vector comprising a polynucleotide comprising an endocarp-specific promoter sequence, or a biologically-active fragment thereof, operably linked to a heterologous nucleotide sequence encoding a product of interest may be a plasmid, a viral vector, a cosmid, or an artificial chromosome. The vector may be a cloning vector, a transcription vector, a shuttle vector, or an expression vector.

In some embodiments, the disclosure relates to a host cell comprising a polynucleotide comprising an endocarp-specific promoter sequence, or a biologically-active fragment thereof, operably linked to a heterologous nucleotide sequence encoding a product of interest. In some embodiments of the disclosure the endocarp-specific promoter comprises a nucleotide sequence at least 90% identical to SEQ ID NO: 1 or a biologically active fragment thereof. The host cell comprising such a polynucleotide may be a plant cell. The plant cell comprising such a polynucleotide may be a drupe cell. The drupe cell comprising such a polynucleotide may be plum, peach, nectarine, apricot, date, mango, cherry, almond, coffee, jujube, oil palm, pistachio, damson, olive, coconut, holly fruit, elder fruit, mulberry, blackberry, or raspberry.

Figure 1:
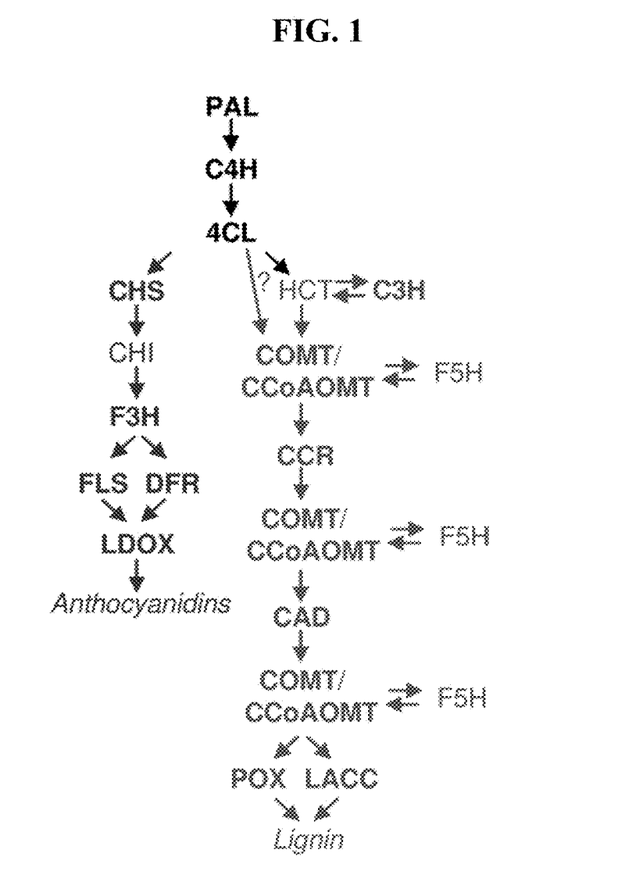
FIG. 1 depicts a schematic of the pathways leading to lignin. PAL: phenylalanine ammonia-lyase; C4H: cinnamate 4-hydroxylase; 4CL: 4-coumarate: CoA ligase; CHS: chalcone synthase; CHI: chalcone isomerase; F3H: flavanone 3-hydrolase; FLS: flavonol synthase; DFR: dihydroflavonol 4-reductase; LDOX: leucoanthocyanidin dioxygenase; HCT: hydroxycinnamoyl-CoA shikimate/Quinatehydroxycinnamoyltransferase; C3H: p-coumarate 3-hydroxylase; COMT/CCoAOMT: caffeoyl-CoA O-methyltransferase; CCR: cinnamoyl CoA reductase; CAD: cinnamyl alcohol dehydrogenase; POX: peroxidase; LACC: a laccase.

In some embodiments of the disclosure, the heterologous nucleotide sequence encoding a product of interest operably linked to an endocarp-specific promoter sequence, or a biologically-active fragment thereof encodes an enzyme active in the lignin biosynthetic pathway, or encodes an RNA hairpin that will prevent expression of a gene in the lignin biosynthetic pathway. Depicted in FIG. 1 is a schematic of the pathways leading to lignin. PAL: phenylalanine ammonia-lyase; C4H: cinnamate 4-hydroxylase; 4CL: 4-coumarate: CoA ligase; CHS: chalcone synthase; CHI: chalcone isomerase; F3H: flavanone 3-hydrolase; FLS: flavonol synthase; DFR: dihydroflavonol 4-reductase; LDOX: leucoanthocyanidin dioxygenase; HCT: hydroxycinnamoyl-CoA shikimate/Quinatehydroxycinnamoyltransferase; C3H: p-coumarate 3-hydroxylase; COMT/CCoAOMT: caffeoyl-CoA O-methyltransferase; CCR: cinnamoyl CoA reductase; CAD: cinnamyl alcohol dehydrogenase; POX: peroxidase; LACC: a laccase.

Figure 2:
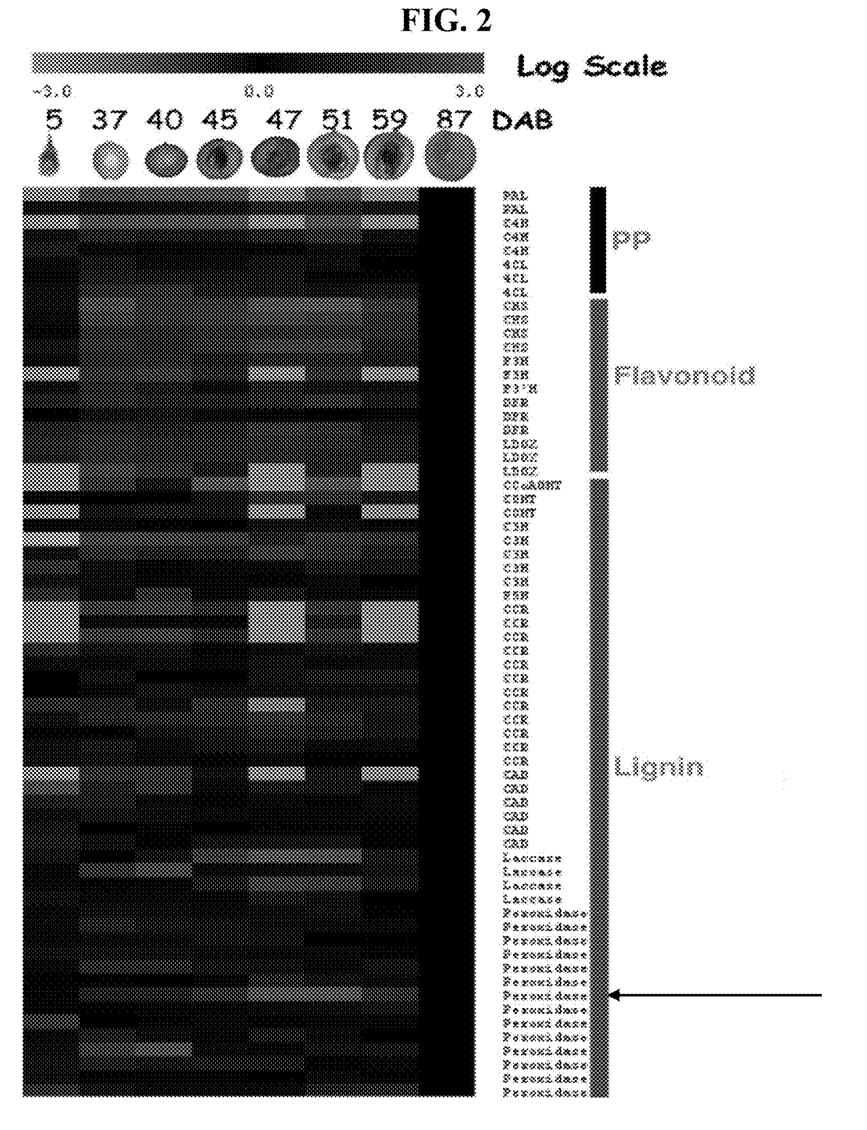
FIG. 2 depicts an image of a microarray heatmap of pathway genes leading to lignin hybridized with RNAs from whole fruit at different days after bloom (DAB). The genes from the phenylpropanoid pathway (PP), the Flavonoid pathway and the Lignin pathway are listed along the side. A Log 2 fold expression scale, developmental times indicated as days after bloom, and a fruit image stained for lignin deposition are shown at the top. Results for the peroxidase gene are indicated by an arrow.

Shown in FIG. 2 is an image of a microarray heatmap of pathway genes leading to lignin hybridized with RNAs from whole fruit at different days after bloom (DAB). The genes from the phenylpropanoid pathway (PP), the Flavonoid pathway, and the Lignin pathway are listed along the side of the heat map. A Log 2 fold expression scale is shown at the top. Developmental times are indicated as days after bloom along with a fruit image stained for lignin deposition. Results for the peroxidase gene are indicated by an arrow.

Figure 3A:
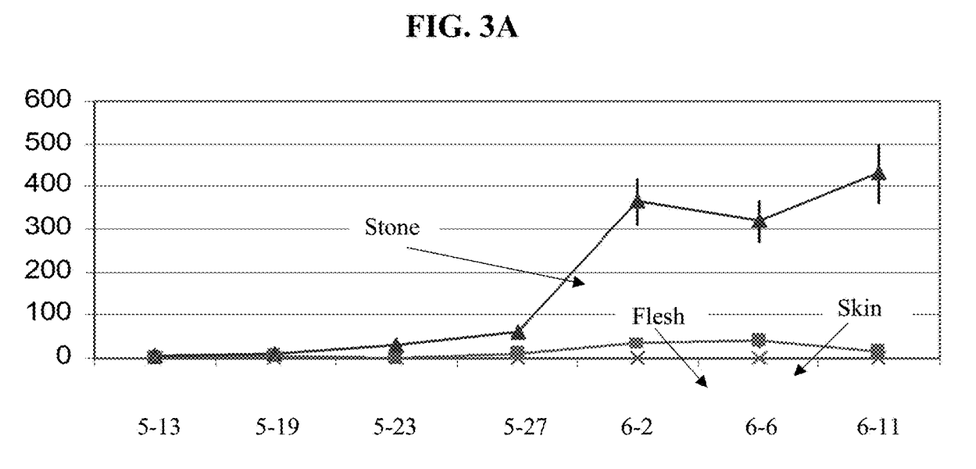
FIG. 3A shows a graph of the relative amount of accumulated POX RNA in stone (endocarp) tissue, skin (exocarp) tissue, and flesh (mesocarp) tissue. The Y Axis indicates the relative amount of POX RNA. The X axis indicates the harvest dates. Filled triangles (▲) show stone data; filled squares (■) show skin data; crossed lines (X) show flesh data.
Figure 3B:
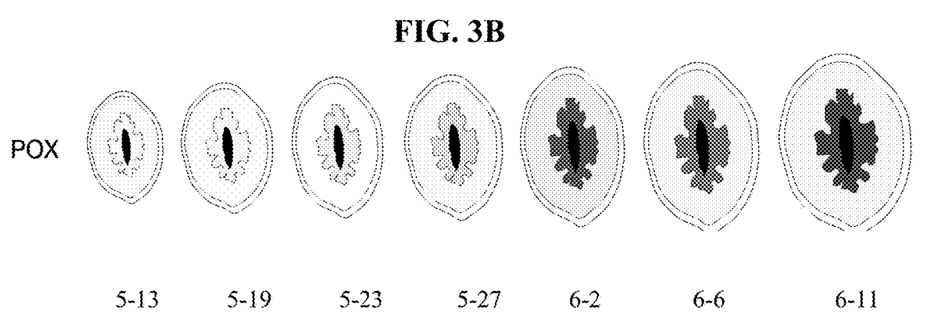
FIG. 3B shows schematic diagrams of peach fruit cross-sections shaded to indicate the amount of POX RNA in the tissues. The darker shading indicates a higher level of expression.
Figure 4:
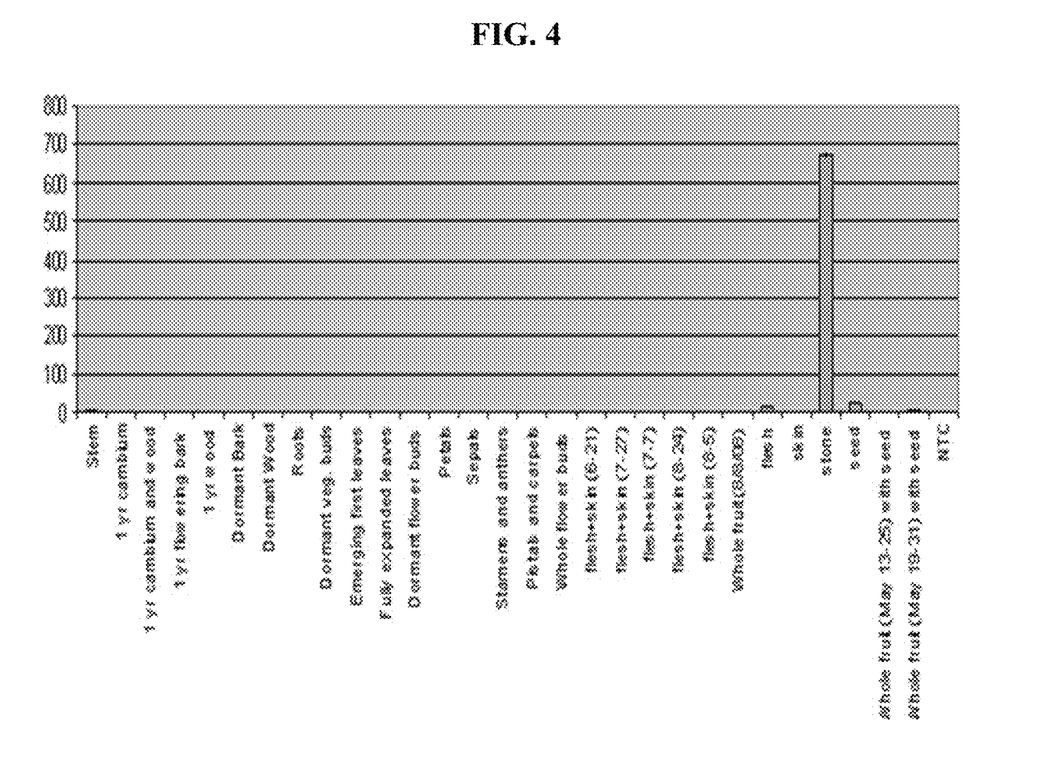
FIG. 4 depicts a graph of the normalized amounts of POX gene expression in flesh (mesocarp), stone (endocarp), skin (exocarp), whole fruit (RC), wood and cambium (Wd+Cb), and seed. The Y axis shows the relative amounts of mRNA based on qPCR results using a relative dilution curve.

Specific tissue was isolated and RNAs extracted to look at the tissue-specific expression of the peroxidase gene indicated by the arrow in the microarray image depicted in FIG. 2. The graph in FIG. 3A depicts the relative amount of POX RNA in stone (endocarp), skin (exocarp), and flesh (mesocarp) tissue from 7 stages of fruit development indicated by the harvest date at the bottom. May 13 is approximately 30 days after bloom (DAB) and June 11 is approximately 59 DAB. At about 59 DAB the stone is quite hard but still able to be cut with a knife. The pictograms of peach fruit shown in FIG. 3B have a black seed surrounded by the irregular shaped stone with the large flesh and narrow band of skin on the outside. Gene expression in each layer is reflected by the intensity of the gray color. The graph in FIG. 4 is a tree anatomy series of tissues to determine the amount of peroxidase gene expression relative to each other. Most tissues had undetectable amounts with stem, fruit, seed and whole fruit during stone hardening period having detectable amounts. Stone tissue at approximately 47 DAB had over 100 times more detectable mRNA for the peroxidase gene.

In an embodiment, the disclosure relates to a method for modifying endocarp development in a fruit of a plant. The method comprising transforming a plant cell with a polynucleotide comprising an endocarp-specific promoter sequence, or a biologically-active fragment thereof, operably linked to a heterologous nucleotide sequence encoding a product of interest, regenerating a plant from the transformed plant cell, and growing the regenerated plant to produce fruit with modified endocarp development. In some embodiments of the disclosure, the fruit has little or no lignin formation.

Figure 5:
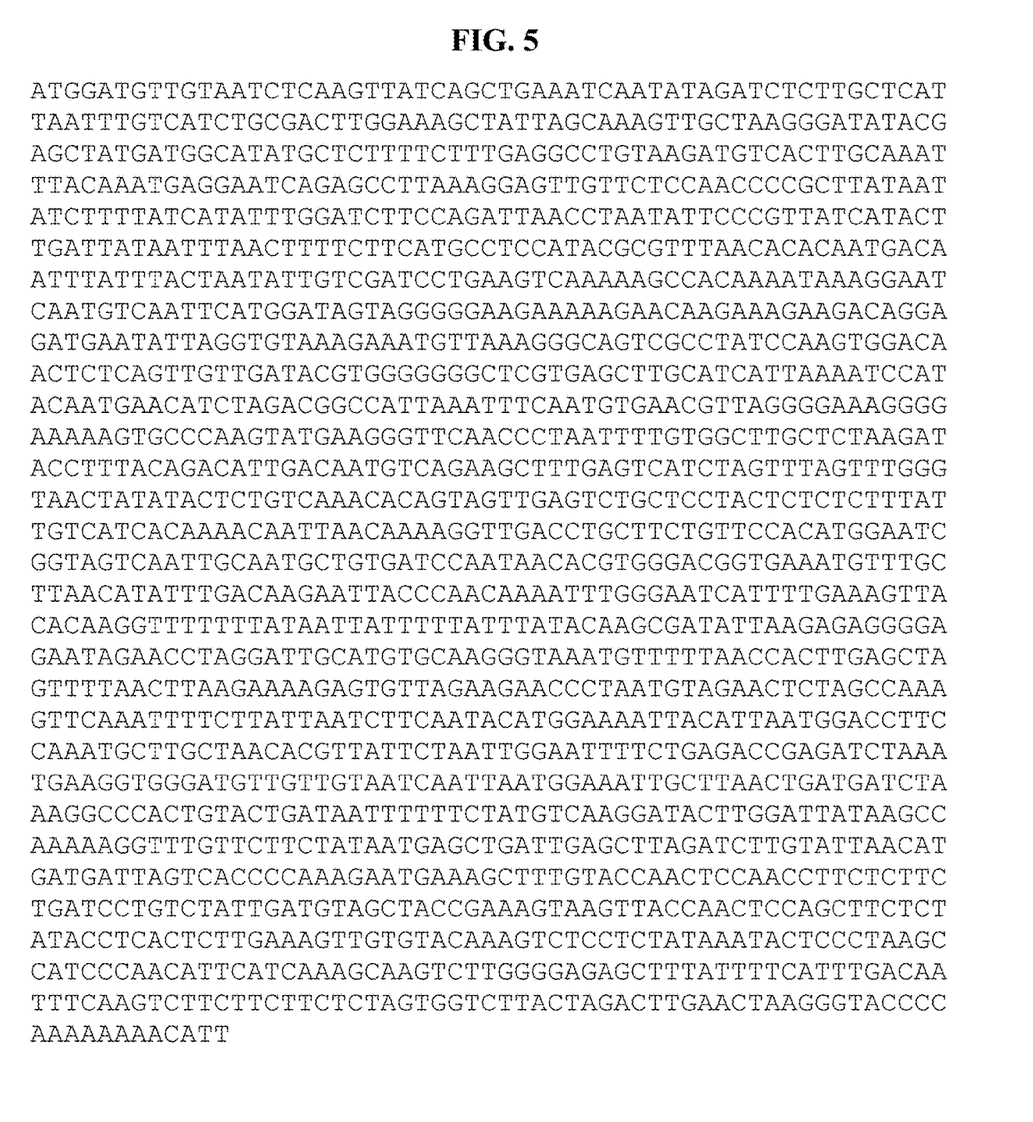
FIG. 5 depicts the nucleotide sequence of the endocarp-specific promoter (POX promoter) identified herein, and set forth in SEQ ID NO: 1.

FIG. 4 depicts a graph of a tree anatomy series of tissues obtained at 47 DAB to determine the amount of peroxidase gene expression relative to each other. Most tissues had undetectable amounts with stem, fruit, seed and whole fruit during stone hardening period having detectable amounts. Stone tissue at approximately 47 DAB had over 100 times more detectable RNA for the peroxidase gene. The amount of POX expression was almost undetectable in woody tissues, and undetectable in stem, bark, roots, vegetative buds, flower buds, petals, sepals, stamens, and anthers. The nucleotide sequence of a newly identified endocarp-specific promoter is set forth in FIG. 5 and in SEQ ID NO: 1.

Figure 6A:
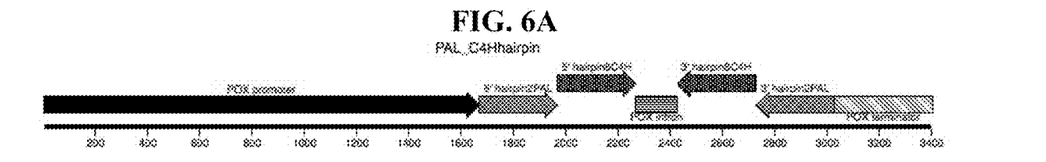
FIG. 6A shows a schematic diagram of STL1, a PAL_C4H hairpin.
Figure 6B:
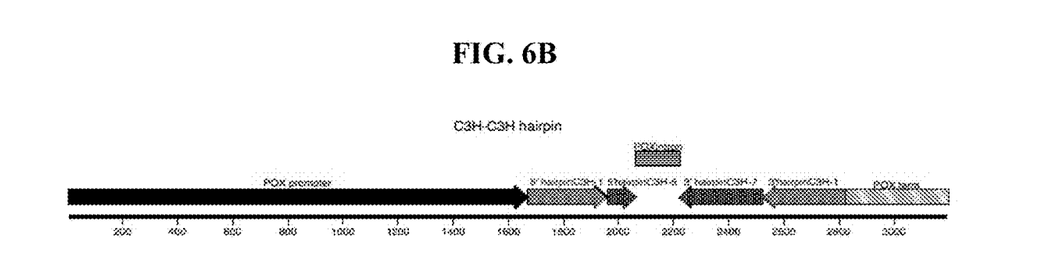
FIG. 6B shows a schematic diagram of STL2, a C3H—C3H hairpin.
Figure 6C:
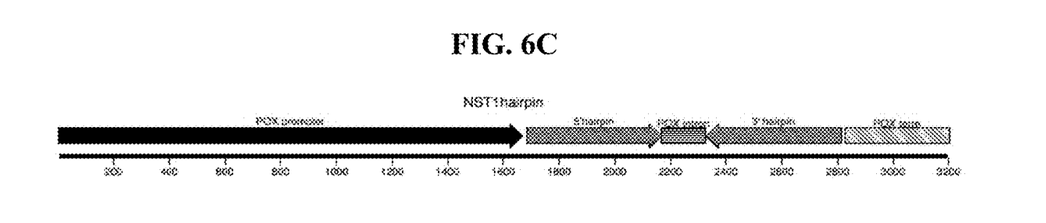
FIG. 6C shows a schematic diagram of STL3, an NST1 hairpin.

The newly identified endocarp-specific promoter was cloned into the pBIN-AFRS vector. Four different heterologous sequences were individually cloned into that vector, such that the POX promoter was driving an UIDA polynucleotide (POX::UIDA), a PAL_C4H hairpin (STL1), a C3H—C3H hairpin (STL2), and an NST1 hairpin (STL3). The three ST constructs containing the POX promoter also contained the POX terminator sequence and the POX::UIDA had the pBIN-AFRS resident ubiquitin (Ubi) terminator. A schematic diagram of the T-DNA region of STL1 construct is shown in FIG. 6A; a schematic diagram of the T-DNA region of STL2 construct is shown in FIG. 6B; and a schematic diagram of the T-DNA region of STL3 construct is shown in FIG. 6C. The POX::UIDA vector will express GUS allowing the identification of the POX promoter expression site. The vector containing the STL1 construct is expected to disrupt the phenylpropanoid pathway. The vector containing the STL2 construct is expected to disrupt the lignin pathway. The vector containing the STL3 construct is expected to interfere with regulation of lignin polymerization.

An *Agrobacterium*-based system using seed-derived hypocotyl tissue was used for plum transformation. Briefly, seeds were cracked out of fully mature pits, and soaked to rehydrate. The hypocotyl tissue was dissected out and sliced into several sections and incubated with *Agrobacterium tumefaciens* carrying the plasmid with the desired T-DNA. After washing off the *Agrobacterium*, hypocotyl slices were placed on a selective media along with antibiotics to kill any *Agrobacterium*. After a series of transfers, regenerating shoots were isolated and placed on rooting media. Plantlets were then transferred to soil and eventually to the greenhouse. Transgenic plants were confirmed with PCRs specific for the inserted gene sequences (Petri, et al., 2008. "High transformation efficiency in plum (*Prunus domestica* L.): a new tool for functional genomics studies in *Prunus* spp.," Mol. Breed, 22: 581-591).

Figure 7:
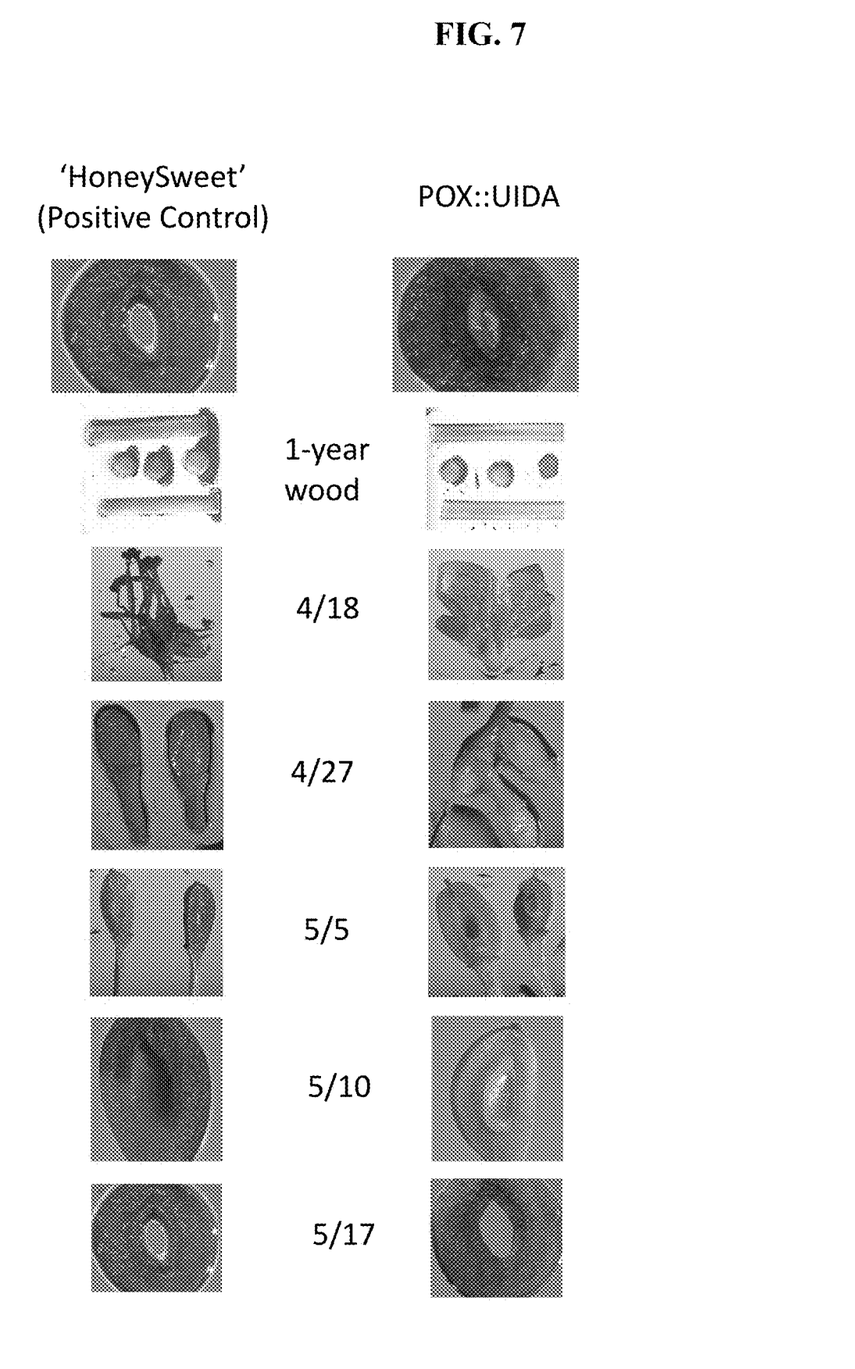
FIG. 7 depict images of 'HoneySweet' and POX::UIDA plants stained for GUS expression. the top row shows photographs of fruit harvested from 8-year-old trees, stained for GUS expression. These images show that fruit from 'HoneySweet presents with an even distribution of positive GUS stain, while fruit expressing POX::UIDA presents positive GUS staining only on the tissue surrounding the stone (endocarp). To ensure that any GUS staining was exposed, the 1-year wood was cut in both dimensions. These images show that there was some light GUS staining on the 'HoneySweet" wood, but no apparent GUS staining on the POX::UIDA wood. The remaining pictures are labeled according to the date in which the fruit was harvested with April 18 representing day 0 DAB-open flowers, and May 25 representing the last week the fruit could be cut through the stone. These pictures show even or almost even distribution of the GUS staining in all 'HoneySweet' tissues, while there was little or no GUS staining in tissues from April 18 and April 27, very light GUS staining in sections of the fruit from May 5 and May 10, and GUS staining localized in the endocarp of POX::UIDA tissues.

The images shown in FIG. 7 show the GUS expression in POX::UIDA or 'HoneySweet' tissues. In FIG. 7, the top row shows photographs of fruit harvested from 8-year-old trees, stained for GUS expression. These images show that fruit from 'HoneySweet' 8 year-old trees presents with an even distribution of positive GUS stain, while most of the GUS staining in fruit expressing POX::UIDA was in the stone. The 1-year wood was cut in both dimensions to expose any GUS staining. These images show that there was some light GUS staining on the 'HoneySweet" wood, but no apparent GUS staining on the POX::UIDA wood. The remaining pictures are labeled according to the date in which the fruit was harvested with April 18 representing day 0 DAB-open flowers, and May 25 representing the last week the fruit could be cut through the stone. These pictures show that the 'HoneySweet' tissues presented even or almost even staining throughout, and the POX::UIDA tissues presented little or no staining on April 18 and April 27, a light staining on May 5 and May 10, and localized staining on May 17.

Figure 8A:
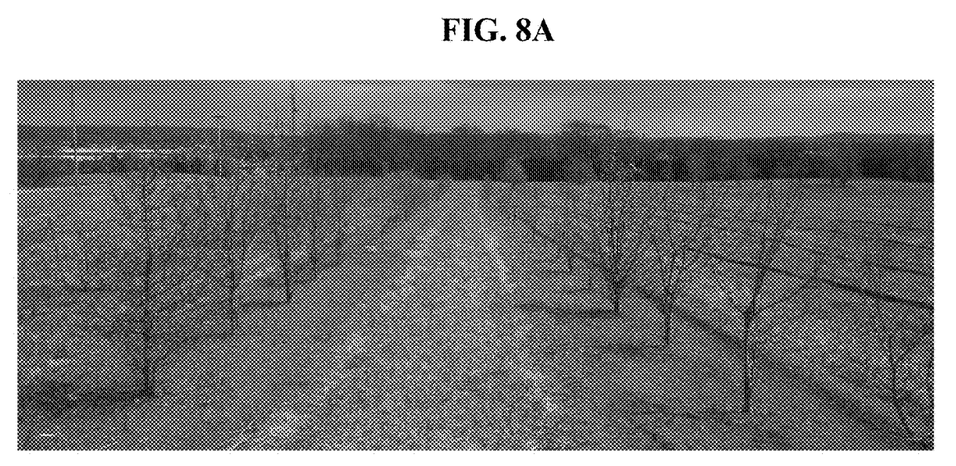
FIG. 8A shows pictures taken during the 2021 spring.
Figure 8B:
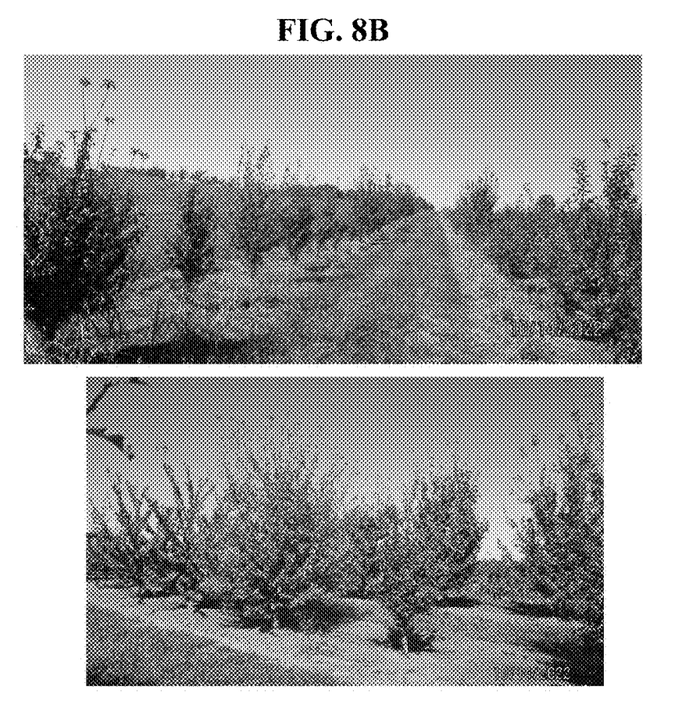
FIG. 8B shows pictures taken during the summer of 2022.
Figure 9A:
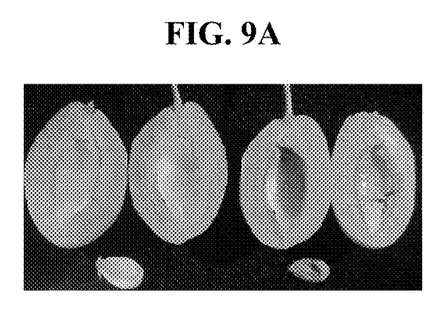
FIG. 9A shows pictures of plums expressing the STL1 construct.
Figure 9B:
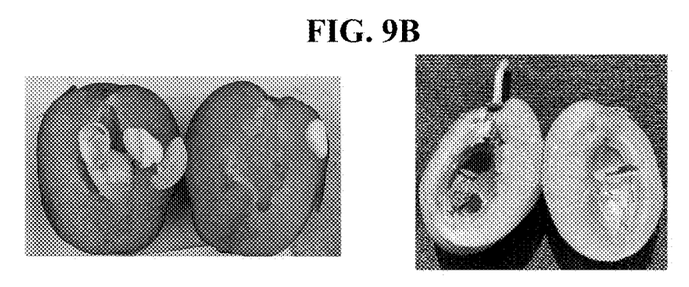
FIG. 9B shows pictures of plums expressing the STL2 construct.
Figure 9C:
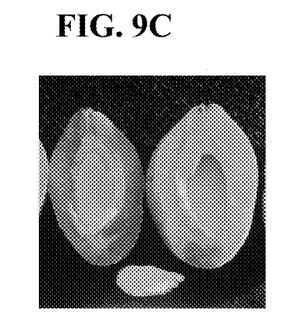
FIG. 9C shows pictures of plants expressing the STL3 construct.

Approximately 160 trees were planted in the field in 2017, all containing the POX promoter. About 40 trees had the POX promoter driving UIDA (POX::UIDA), about 40 trees had the POX promoter driving a phenylpropanoid pathway gene hairpin (STL1), about 40 trees had a POX promoter driving a lignin pathway gene hairpin (STL2), and about 40 trees had a POX promoter driving a lignin polymerization transcription factor gene hairpin (STL3). All trees showed normal growth throughout that time as seen in the spring of 2021 (FIG. 8A) and summer of 2022 (FIG. 8B). Some of the Plums expressing the STL1, STL2, or STL3 constructs show stone defects. These three constructs (STL1, STL2 and STL3) represent blocks at three different places leading to the hardened-polymerized lignin. The Phenylpropanoid pathway feeds precursors to the lignin pathway (ST1), the formation of lignin monomers (ST2), and the polymerization regulation initiates the hardening when the lignin monomers polymerize (ST3). Pictures of plums with noticeable stone defects are shown, those expressing the STL1 construct are shown in FIG. 9A, pictures of plums expressing the STL2 construct are shown in FIG. 9B, and pictures of plums expressing the STL3 construct are shown in FIG. 9C. All the plums in the images shown in FIG. 9A to FIG. 9C show stone defects.

Embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

As used herein, the term "about" is defined as plus or minus ten percent of a recited value. For example, about 1.0 g means 0.9 g to 1.1 g.

As used herein, the terms "promoter" and "promoter sequence" are used interchangeably and refer to a DNA polynucleotide that defines where, when, and how much transcription of a gene by RNA polymerase begins. Promoters are typically located directly upstream or at the 5' end of the transcription initiation site. RNA polymerase and the necessary transcription factors bind to the promoter sequence and initiate transcription. Promoter sequences define the direction of transcription and indicate which DNA strand will be transcribed.

The term "chimeric" is used herein to describe polynucleotides or genes, or constructs wherein at least two of the elements of the polynucleotide or gene or construct, such as the promoter and the polynucleotide to be transcribed and/or other regulatory sequences and/or filler sequences and/or complements thereof are heterologous to each other.

As used herein, the term "heterologous polynucleotides" refers to polynucleotides that are not found in nature operatively linked to each other or that in nature are not contiguous to each other. For example, a promoter described herein is considered heterologous to an *Arabidopsis* coding region sequence. A peach peroxidase promoter is considered heterologous to a polynucleotide encoding a peroxidase from other stone fruit. Similarly, a peroxidase promoter is heterologous to other genes from the phenylpropanoid pathway.

Regulatory element sequences, such as untranslated regions (UTRs) or 3' end termination sequences that do not originate in nature from the same gene as the coding sequence, are considered heterologous to the coding sequence. Elements operatively linked in nature and contiguous to each other are not heterologous to each other. On the other hand, these same elements remain operatively linked but become heterologous if a filler sequence is added between them. Thus, the promoter and coding sequences of a peach gene expressing a peroxidase are not heterologous to each other, but the promoter and coding sequence of a peach gene operatively linked in a novel manner are heterologous.

As used herein, a "homologous" polynucleotide refers to a polynucleotide that shares sequence similarity with the polynucleotide of interest. This similarity may be in only a fragment of the sequence and often represents a functional domain such as, examples including, without limitation, a DNA binding domain or a domain with tyrosine kinase activity. The functional activities of homologous polynucleotides are not necessarily the same.

As used herein, a promoter sequence or promoter control element is "operably linked" to a heterologous nucleic acid molecule in such a way as to place transcription of the heterologous nucleic acid molecule under the influence or control of the promoter or promoter control element. Two polynucleotide sequences (such as a promoter linked to the 5'-end of a heterologous nucleic aid molecule to be transcribed) are said to be operably linked if induction of promoter function results in the transcription of mRNA encoding the heterologous nucleic acid and if the nature of the linkage between the two DNA sequences does not (1) result in the introduction of a frame-shift mutation, (2) interfere with the ability of the promoter sequence to direct the expression of the polypeptide, antisense RNA, RNAi, or ribozyme, or (3) interfere with the ability of the polynucleotide template to be transcribed. Thus, a promoter sequence would be operably linked to a heterologous nucleic acid molecule sequence if the promoter was capable of effecting transcription of that heterologous nucleic acid sequence.

As used herein, the term "percent sequence identity" refers to the degree of identity between any given query sequence, e.g., the polynucleotide of SEQ ID NO:1 and a subject sequence. A subject sequence typically has a length that is from about 80 percent to 150 percent of the length of the query sequence, e.g., 82, 85, 87, 89, 90, 93, 95, 97, 99, 100, 105, 110, 115, or 120, 130, 140, or 150 percent of the length of the query sequence. A query nucleic acid sequence is aligned to one or more subject nucleic acid sequences using the computer program ClustalW (version 1.83, default parameters), which allows alignments of nucleic acid or protein sequences to be carried out across their entire length (global alignment).

The nucleic acid sequence set forth in SEQ ID NO:1 is an example of a POX promoter sequence provided herein. However, a POX promoter can have a nucleotide sequence that deviates from that set forth in SEQ ID NO:1, while retaining the ability to direct expression of an operably-linked heterologous nucleic acid molecule. For example, a promoter having at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to the nucleotide sequence set forth in SEQ ID NO:1 can direct endocarp-specific expression of an operably linked heterologous nucleotide sequence encoding a product of interest.

A promoter can also be a fragment of the nucleic acid sequence set forth in SEQ ID NO:1, while retaining promoter activity, i.e., the ability to direct expression of an operably linked heterologous nucleic acid molecule.

The terms "endocarp-specific promoter" and "stone-specific promoter" are used interchangeably herein, and refer to a promoter that has a high preference for modulating transcript levels in an endocarp or stone. By "high preference" is meant at least 1.5 fold, at least 2 fold, at least 3-fold, at least 5-fold, at least 10-fold, at least 20-fold, at least 50-fold, or at least 100-fold increase in transcript levels under the specific condition over the transcription under any other reference condition considered.

All publications, patents, and patent applications mentioned in this specification are herein incorporated by reference to the same extent as if each individual publication, patent, or patent application was specifically and individually indicated to be incorporated by reference.

EXAMPLES

Having now generally described this invention, the same will be better understood by reference to certain specific examples, which are included herein only to further illustrate the invention and are not intended to limit the scope of the invention as defined by the claims.

Example 1

Identification and Cloning of Peroxidase Gene Promoter

The tissue specific expression of the peach peroxidase (POX) gene was determined, and an endocarp-specific promoter driving expression of the POX gene was identified and cloned.

The peach POX gene was identified through gene expression profiling (C. D. Dardick, et al., 2010, "Stone formation in peach fruit exhibits spatial coordination of the lignin and flavonoid pathways and similarity to *Arabidopsis* dehiscence," BMC Biology 8:13, http://www.biomedcentral.com/1741-7007/8/13). RNAs were extracted from whole fruit from 5 to 59 days after bloom (DAB). Genes associated with the production of the lignified endocarp were expression profiled, specifically genes in the three major metabolic pathways (flavonoid biosynthesis, lignin biosynthesis, and the phenylpropanoid pathway). Depicted in FIG. 1 is a schematic of the genes forming part of these three major metabolic pathways. FIG. 2 shows a heat map of for all significant genes in these pathways, with an arrow indicating the location of the data for the peroxidase (POX) gene. At 59 DAB stone hardening had begun, and it was not possible to cut through the stone with a knife after this day.

The graph in FIG. 3A shows the levels of peroxidase gene (POX) in stone, skin and flesh at 7 stages of fruit development indicated by the harvest date at the bottom. May 13 is approximately 30 days after bloom (DAB) and June 11 is approximately 59 DAB. At 59 DAB the stone is quite hard but still able to be cut with a knife. This figure shows that the POX gene was highly enriched in the endocarp tissue. The pictograms of peach fruit shown in FIG. 3B have a black seed surrounded by the irregular shaped stone with the large flesh and narrow band of skin on the outside. Gene expression in each layer is reflected by the intensity of the gray color. The graph in FIG. 4 is a tree anatomy series of tissues obtained at 47 DAB to determine the amount of peroxidase gene expression relative to each other. Most tissues had undetectable amounts with stem, fruit, seed and whole fruit during stone hardening period having detectable amounts. Stone tissue at approximately 47 DAB had over 100 times more detectable RNA for the peroxidase gene. The amount of POX expression was almost undetectable in woody tissues, and undetectable in stem, bark, roots, vegetative buds, flower buds, petals, sepals, stamens, and anthers.

To identify the promoter driving POX expression, primers were initially designed from a number of published sequences to amplify the nucleotide sequence of the POX gene. The newly designed primers were used to search the peach genome Version 1, where only the nucleotide sequence of the ppa008349 gene was amplified. The upstream region of this gene was then scanned to find good promoting sequences based on the potential CIS binding site of various transcription factors. A 1,700 base pair polynucleotide fragment upstream of the translational start codon of the POX gene was identified as the putative promoter sequence, synthesized, and cloned into a vector. The nucleotide sequence of a newly identified endocarp-specific promoter is set forth in FIG. 5 and in SEQ ID NO: 1. The 1,700 bp putative POX gene promoter was synthesized with BamH I and Sal I restriction endonuclease sites to facilitate removal from the original plasmid and cloning the promoter sequence into the pBIN-AFRS plasmid.

The information given in this example discloses the identification and cloning of an endocarp-specific promoter polynucleotide.

Example 2

Transformation of Plants with the POX Promoter

The endocarp-specific promoter sequence identified above, was used to drive various hairpin sequences of genes from the lignin pathway, or UIDA for GUS expression.

The polynucleotide comprising the newly identified endocarp-specific promoter was excised from the pJ201 vector using the synthesized end sites, and cloned into the pBIN-AFRS vector. Four different heterologous sequences were individually cloned into that vector, such that the POX promoter was driving an UIDA polynucleotide (POX::UIDA), a PAL_C4H hairpin (STL1), a C3H—C3H hairpin (STL2), and an NST1 hairpin (STL3). The three ST constructs containing the POX promoter also contained the POX terminator sequence and the POX::UIDA had the pBIN-AFRS resident ubiquitin (Ubi) terminator. A schematic diagram of the T-DNA region of STL1 construct is shown in FIG. 6A; a schematic diagram of the T-DNA region of STL2 construct is shown in FIG. 6B; and a schematic diagram of the T-DNA region of STL3 construct is shown in FIG. 6C. The POX::UIDA vector will express GUS allowing the identification of the POX promoter expression site. The vector containing the STL1 construct is expected to disrupt the phenylpropanoid pathway. The vector containing the STL2 construct is expected to disrupt the lignin pathway. The vector containing the STL3 construct is expected to interfere with regulation of lignin polymerization.

The plum transformation system is an *Agrobacterium*-based system using seed-derived hypocotyl tissue. Briefly, seeds were cracked out of fully mature pits, and soaked to rehydrate. The hypocotyl tissue was dissected out and sliced into several sections and incubated with *Agrobacterium tumefaciens* carrying the plasmid with the desired T-DNA. After washing off the *Agrobacterium*, hypocotyl slices were placed on a selective media along with antibiotics to kill any *Agrobacterium*. After a series of transfers, regenerating shoots were isolated and placed on rooting media. Plantlets were then transferred to soil and eventually to the greenhouse. Transgenic plants were confirmed with PCRs specific for the inserted gene sequences (Petri, C., et al., 2008, "High transformation efficiency in plum (*Prunus domestica* L.): a new tool for functional genomics studies in *Prunus* spp.," Mol. Breed. 22: 581-591).

'HoneySweet' plum was used as positive control for GUS staining. It has a UIDA gene driven by a 35S promoter that is constitutively expressed in most tissues. Plums labeled POX::UIDA were transformed with a vector containing the POX promoter driving expression of the UIDA sequence followed by the Ubi terminator sequence. About ten independent plum (*Prunus domestica*) transformants were identified in tissue culture and approximately 10 plants were regenerated from each. These lines were grown to a few feet in the greenhouse, and then put in the field under APHIS permits. Over the course of growth, various tissues such as flower, leaf, and woody twigs were subjected to GUS assays for the UIDA gene activity, and all were consistently negative. In the spring of 2022, the transgenic trees bloomed and set fruit. Fruits were collected at various dates to look for expression of the peroxidase gene promoter-driven UIDA gene. Approximately 2 weeks prior to stone hardening, GUS staining was clearly visible only within the endocarp. This is consistent with previous Peroxidase gene expression assays and indicated that the selected promoter could be successfully used to target gene expression specifically within the endocarp. This will enable the use of genes to block endocarp formation and/or lignification and create pitless stone fruit without negative impacts on other tissues within the tree.

The images shown in FIG. 7 show the GUS expression in POX::UIDA or 'HoneySweet' tissues. In FIG. 7, the top row shows photographs of fruit harvested from 8-year-old trees, stained for GUS expression. These images show that fruit from 'HoneySweet' 8 year-old trees presents with an even distribution of positive GUS stain, while most of the GUS staining in fruit expressing POX::UIDA was in the stone. The 1-year wood was cut in both dimensions to expose any GUS staining. These images show that there was some light GUS staining on the 'HoneySweet" wood, but no apparent GUS staining on the POX::UIDA wood. The remaining pictures are labeled according to the date in which the fruit was harvested with April 18 representing day 0 DAB-open flowers, and May 25 representing the last week the fruit could be cut through the stone. These pictures show that the 'HoneySweet' tissues presented even or almost even staining throughout, and the POX::UIDA tissues presented little or no staining on April 18 and April 27, a light staining on May 5 and May 10, and localized staining on May 17.

Approximately 160 trees were planted in the field in 2017, all containing the POX promoter. About 40 trees had the POX promoter driving UIDA (POX::UIDA), about 40 trees had the POX promoter driving a phenylpropanoid pathway gene hairpin (STL1), about 40 trees had a POX promoter driving a lignin pathway gene hairpin (STL2), and about 40 trees had a POX promoter driving a lignin polymerization transcription factor gene hairpin (STL3). All trees showed normal growth throughout that time as seen in the spring of 2021 (FIG. 8A) and summer of 2022 (FIG. 8B). Some of the Plums expressing the STL1, STL2, or STL3 constructs show stone defects. These three constructs (STL1, STL2 and STL3) represent blocks at three different places leading to the hardened-polymerized lignin. The Phenylpropanoid pathway feeds precursors to the lignin pathway (ST1), the formation of lignin monomers (ST2), and the polymerization regulation initiates the hardening when the lignin monomers polymerize (ST3). Pictures of plums with noticeable stone defects are shown, those expressing the STL1 construct are shown in FIG. 9A, pictures of plums expressing the STL2 construct are shown in FIG. 9B, and pictures of plums expressing the STL3 construct are shown in FIG. 9C. All the plums in the images shown in FIG. 9A to FIG. 9C show stone defects.

The information given in this example shows that the POX promoter drives gene expression specifically in the endocarp, without any negative impacts on other tissues. Similarly, transgenic plants expressing hairpin structures expected to disrupt the phenylpropanoid pathway, the lignin pathway, or interfere with regulation of lignin polymerization produced fruit with stone defects.

We claim:

1. A polynucleotide comprising an endocarp-specific promoter sequence at least 99% identical to SEQ ID NO: 1 operably linked to a heterologous nucleotide sequence encoding a product of interest.

2. The polynucleotide of claim 1, wherein the product of interest is an RNA molecule or a polypeptide.

3. The polynucleotide of claim 1, wherein the product of interest is in the lignin pathway.

4. The polynucleotide of claim 1, wherein the product of interest blocks at least one of formation of phenylpropanoid pathway lignin-pathway precursors, formation of lignin monomers, or polymerization of the lignin monomers.

5. A vector comprising the polynucleotide of claim 1.

6. A host cell comprising the polynucleotide of claim 1.

7. A plant or plant part comprising the polynucleotide of claim 1.

8. The plant or plant part of claim 7, wherein the plant is a drupe.

9. The plant or plant part of claim 8, wherein the drupe is plum, peach, nectarine, apricot, date, mango, cherry, almond, coffee, jujube, oil palm, pistachio, damson, olive, coconut, holly fruit, elder fruit, mulberry, blackberry, or raspberry.

10. The polynucleotide of claim 1, wherein the heterologous nucleotide sequence encoding a product of interest is a negative regulator of endocarp development and/or lignification.

11. A host cell comprising the polynucleotide of claim 10.

12. A plant or plant part comprising the polynucleotide of claim 10.

13. A method for modifying endocarp development in a fruit of a plant, the method comprising:
transforming a plant cell with the polynucleotide of claim 1,
regenerating a plant from the transformed plant cell, and
growing the regenerated plant to produce fruit with modified endocarp development.

14. The method of claim 13, wherein the product of interest is an RNA molecule or a polypeptide.

15. The method of claim 13, wherein the product of interest blocks at least one of formation of phenylpropanoid pathway lignin-pathway precursors, formation of lignin monomers, or polymerization of the lignin monomers.

16. The method of claim 13, wherein fruit from the transformed plant has less lignin formation as compared to fruit from a non-transformed plant.

17. The method of claim 13, wherein the plant is a drupe.

18. The method of claim 17, wherein the drupe is plum, peach, nectarine, apricot, date, mango, cherry, almond, coffee, jujube, oil palm, pistachio, damson, olive, coconut, holly fruit, elder fruit, mulberry, blackberry, or raspberry.

* * * * *